US008548582B2

(12) United States Patent
McDonald et al.

(10) Patent No.: US 8,548,582 B2
(45) Date of Patent: Oct. 1, 2013

(54) SYSTEMS AND METHODS FOR ELECTRICALLY DISCONNECTING COMPONENTS OF IMPLANTABLE ELECTRICAL SYSTEMS

(75) Inventors: Matthew Lee McDonald, Pasadena, CA (US); Ross Daniel Venook, Millbrae, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 13/531,098

(22) Filed: Jun. 22, 2012

(65) Prior Publication Data

US 2013/0006316 A1    Jan. 3, 2013

Related U.S. Application Data

(60) Provisional application No. 61/503,418, filed on Jun. 30, 2011.

(51) Int. Cl.
 *A61N 1/36* (2006.01)
(52) U.S. Cl.
 USPC ............................................................ 607/2
(58) Field of Classification Search
 USPC ............................................................ 607/2
 See application file for complete search history.

(56) References Cited

U.S. PATENT DOCUMENTS

| | | | |
|---|---|---|---|
| 6,181,969 B1 | 1/2001 | Gord | |
| 6,321,126 B1 * | 11/2001 | Kuzma | 607/137 |
| 6,516,227 B1 | 2/2003 | Meadows et al. | |
| 6,609,029 B1 | 8/2003 | Mann et al. | |
| 6,609,032 B1 | 8/2003 | Woods et al. | |
| 6,741,892 B1 | 5/2004 | Meadows et al. | |
| 7,244,150 B1 | 7/2007 | Brase et al. | |
| 7,437,193 B2 | 10/2008 | Parramon et al. | |
| 7,672,734 B2 | 3/2010 | Anderson et al. | |
| 7,761,165 B1 | 7/2010 | He et al. | |
| 7,803,021 B1 * | 9/2010 | Brase | 439/668 |
| 7,949,395 B2 | 5/2011 | Kuzma | |
| 7,962,224 B1 * | 6/2011 | Blischak | 607/116 |
| 7,974,706 B2 | 7/2011 | Moffitt et al. | |
| 8,046,073 B1 * | 10/2011 | Pianca | 607/37 |

(Continued)

OTHER PUBLICATIONS

Nyenhuis, J.A. et al., "MRI and implantable medical devices: basic interations with an emphasis on heating," IEEE Transactions on Device and Materials Reliability, vol. 5, No. 3, 2005, pp. 467-480.

(Continued)

*Primary Examiner* — George Manuel
(74) *Attorney, Agent, or Firm* — Frommer Lawrence & Haug LLP; Patrick R. Turner

(57) ABSTRACT

An implantable electrical stimulation system includes a control module electrically coupleable to a lead. The control module includes a housing, an electronic subassembly disposed in the housing, and a connector assembly for receiving the lead. The connector assembly includes a port for receiving a proximal end of the lead. Connector contacts are disposed in the connector assembly housing and electrically couple to the electronic subassembly. The connector contacts align with terminals disposed on the lead to form an electrical connection between the connector contacts and the terminals when the proximal end of the lead is disposed in the port of the connector assembly. A disconnecting feature includes a switch for electrically disabling, or at least significantly reducing, the electrical connection between the connector contacts and the electronic subassembly when the switch is opened.

20 Claims, 7 Drawing Sheets

(56) References Cited

U.S. PATENT DOCUMENTS

| | | |
|---|---|---|
| 8,175,710 B2 | 5/2012 | He |
| 2005/0165465 A1 | 7/2005 | Pianca et al. |
| 2007/0150036 A1 | 6/2007 | Anderson |
| 2008/0071320 A1 | 3/2008 | Brase |

OTHER PUBLICATIONS

Rezai, A.R. et al., "Neurostimulation system used for deep brain stimulation (DBS): MR safety issues and implications of failing to follow safety recommendations," Investgative Radiology, vol. 39, No. 5, 2004, pp. 300-303.

* cited by examiner

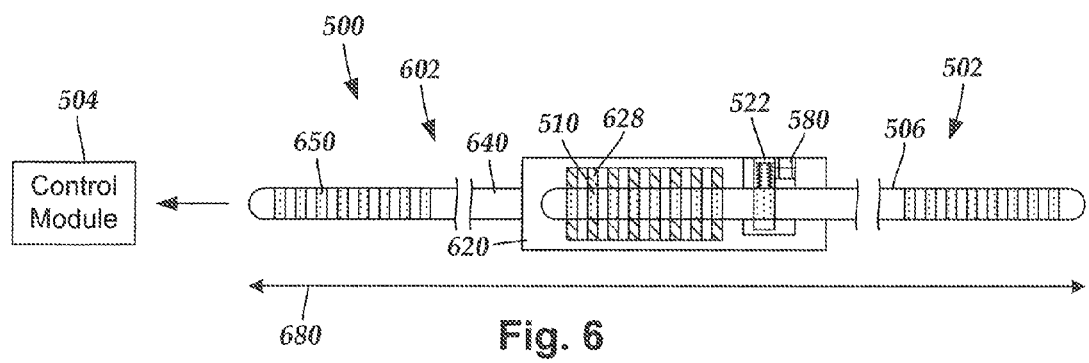
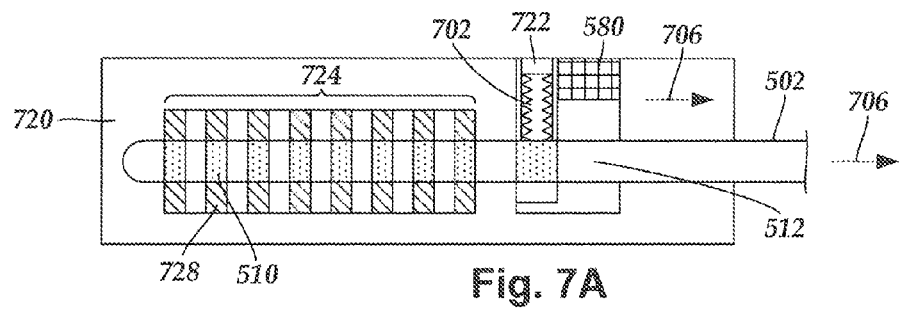
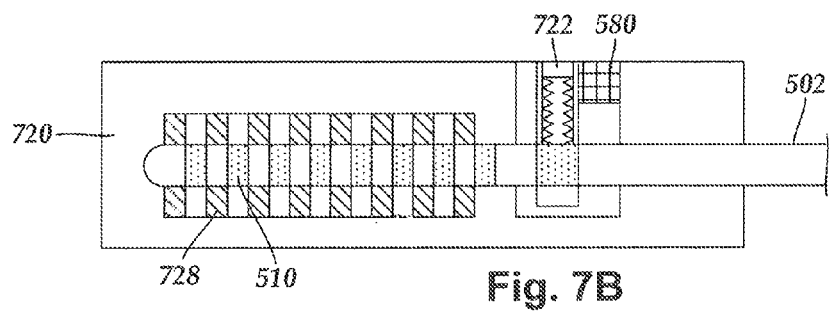

SYSTEMS AND METHODS FOR ELECTRICALLY DISCONNECTING COMPONENTS OF IMPLANTABLE ELECTRICAL SYSTEMS

CROSS-REFERENCE TO RELATED APPLICATIONS

This application claims the benefit under 35 U.S.C. §119 (e) of U.S. Provisional Patent Application Ser. No. 61/503,418 filed on Jun. 30, 2011, which is incorporated herein by reference.

FIELD

The present invention is directed to the area of implantable electrical systems and methods of making and using the systems. The present invention is also directed to implantable electrical systems having components that can be electrically disconnected from one another, as well as methods of making and using the implantable electrical systems.

BACKGROUND

Implantable electrical systems, such as implantable electrical stimulation systems, have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

Conventional implanted electrical stimulation systems are often incompatible with magnetic resonance imaging ("MRI") due to the large radio frequency ("RF") pulses, as well as 'gradient' or audio frequency pulses used during an MRI procedure. The RF pulses and gradient signals can generate transient signals in the conductors and electrodes of an implanted lead. These signals can have deleterious effects including, for example, unwanted heating of the tissue causing tissue damage, induced currents in the lead, or premature failure of electronic components.

BRIEF SUMMARY

In one embodiment, an implantable electrical stimulation system includes a lead having a lead body with a distal end and a proximal end. A plurality of electrodes are disposed on the distal end of the lead body. A plurality of terminals are disposed on the proximal end of the lead body. A plurality of conductors extend along a longitudinal length of the lead body and electrically couple at least one of the electrodes to at least one of the terminals. A control module is configured and arranged to electrically couple to the lead. The control module includes a housing, an electronic subassembly disposed in the housing, and a connector assembly for receiving the lead body. The connector assembly includes a connector assembly housing defining a port configured and arranged for receiving the proximal end of the lead body. A plurality of connector contacts are disposed in the connector assembly housing and electrically couple to the electronic subassembly. The plurality of connector contacts are configured and arranged to align with the plurality of terminals such that an electrical connection is formed between the plurality of connector contacts and the plurality of terminals when the proximal end of the lead body is disposed in the port of the connector assembly. A disconnecting feature includes a switch configured and arranged to electrically disable, or at least significantly reduce, the electrical connection between the plurality of connector contacts and the electronic subassembly when the switch is opened.

In another embodiment, an implantable electrical stimulation system includes a lead having a lead body with a distal end and a proximal end. A plurality of electrodes are disposed on the distal end of the lead body. A plurality of terminals are disposed on the proximal end of the lead body. A plurality of conductors extend along a longitudinal length of the lead body and electrically couple at least one of the electrodes to at least one of the terminals. A control module is configured and arranged to electrically couple to the lead. The control module includes a housing, an electronic subassembly disposed in the housing, and a connector assembly for receiving the lead body. The connector assembly includes a connector assembly housing defining a port configured and arranged for receiving the proximal end of the lead body. A connector block is disposed in the connector housing. The connector block includes a plurality of connector contacts configured and arranged to align with the plurality of terminals of the lead such that an electrical connection is formed between the plurality of connector contacts and the plurality of terminals when the proximal end of the lead body is disposed in the port of the connector assembly. A disconnecting feature is configured and arranged to mechanically move the proximal end of the lead body relative to the connector block to misalign the plurality of connector contacts from the plurality of terminals to sever, or at least significantly reduce, the electrical connection between the plurality of connector contacts and the plurality of terminals.

In yet another embodiment, a method of reducing susceptibility of an electrical stimulation system to undesired electromagnetic irradiation includes inserting a lead into a connector assembly electrically coupled to a control module. The lead includes a lead body having a plurality of electrodes disposed on a distal end of the lead body, a plurality of terminals disposed on a proximal end of the lead body, and a plurality of conductors electrically coupling at least one of the electrodes to at least one of the terminals. The connector assembly includes a connector assembly housing defining a port. The port receives the proximal end of the lead body when the lead is inserted into the connector assembly. A connector block is disposed in the connector housing. The connector block includes a plurality of connector contacts that align with the plurality of terminals such that an electrical connection is formed between the plurality of connector contacts and the plurality of terminals when the lead is inserted into the connector assembly. A retention sleeve of the lead is fastened to a retention block of the connector assembly. The retention block is configured and arranged to move relative to the connector block. The proximal end of the lead body is mechanically moved relative to the connector block using a disconnecting feature. The mechanical movement misaligns the plurality of connector contacts from the plurality of terminals to sever, or at least significantly reduce, the electrical connection between the plurality of connector contacts and the plurality of terminals.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 6 is a schematic view of one embodiment of the disconnecting feature of FIG. 5A disposed on a connector assembly of a lead extension disposed between the lead of FIG. 5A and the control module of FIG. 5A, according to the invention;

FIG. 7A is a schematic side view of one embodiment of the disconnecting feature of FIG. 5A disposed on a connector assembly into which one end of the lead of FIG. 5A is disposed, the disconnecting feature is in a de-activated position such that current is enabled to propagate between the lead and the connector assembly, according to the invention;

FIG. 7B is a schematic side view of one embodiment of the disconnecting feature of FIG. 5A transitioned to an activated position, the transition mechanically moving the lead of FIG. 5A relative the connector assembly of FIG. 7A to electrically disconnect the lead from the connector assembly, thereby disrupting current flow between the lead and the connector assembly, according to the invention;

DETAILED DESCRIPTION

The present invention is directed to the area of implantable electrical systems and methods of making and using the systems. The present invention is also directed to implantable electrical systems having components that can be electrically disconnected from one another, as well as methods of making and using the implantable electrical systems.

Suitable implantable electrical systems can include, for example, electrical stimulation systems. Suitable implantable electrical stimulation systems include, but are not limited to, an electrode lead ("lead") with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,244,150; 7,672,734; 7,761,165; 7,949,395; 7,974,706; and 8,175,710; and U.S. Patent Applications Publication Nos. 2005/0165465 and 2007/0150036, all of which are incorporated by reference.

Figure 1:
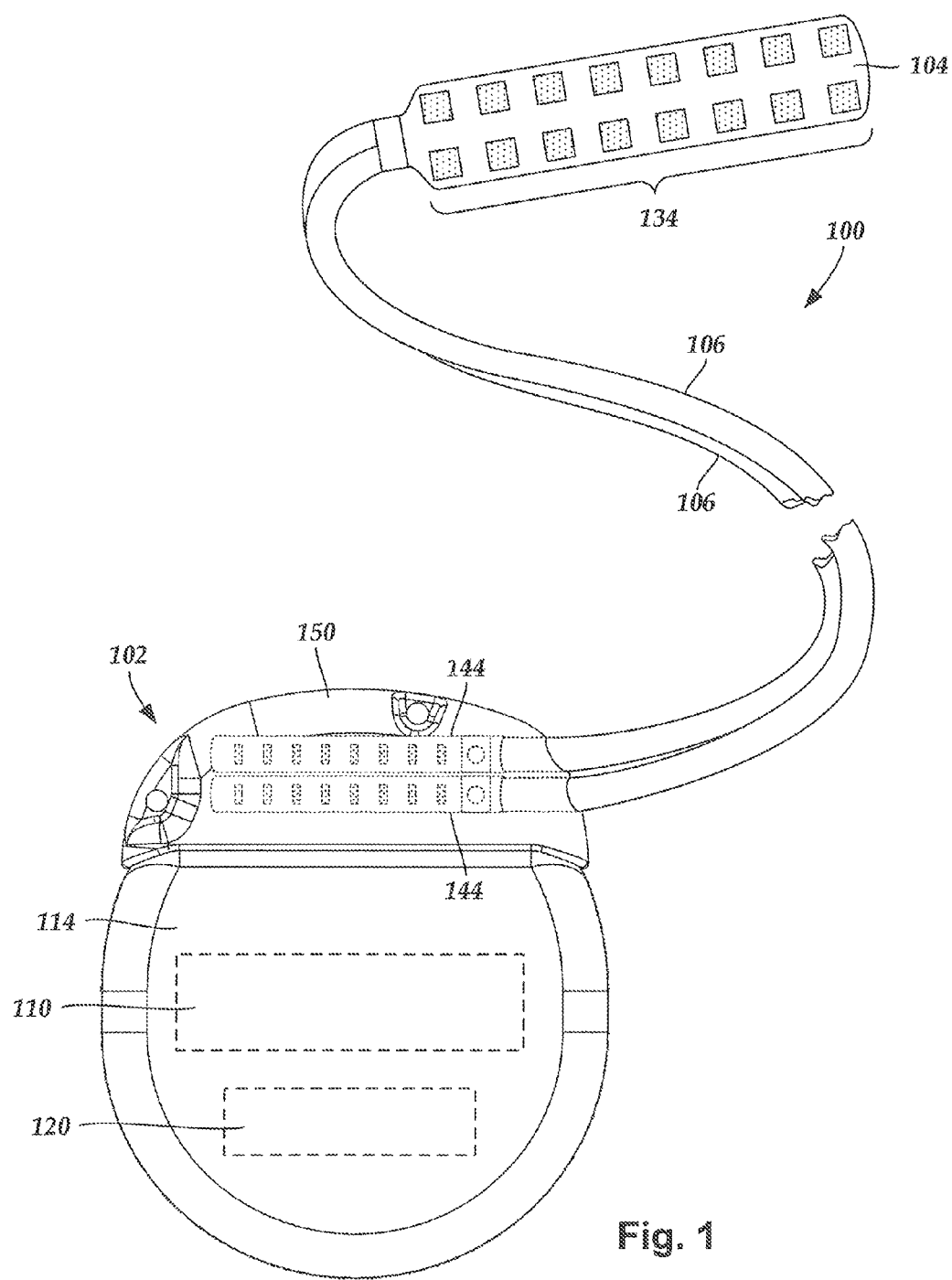
FIG. 1 is a schematic view of one embodiment of an electrical stimulation system that includes a paddle body coupled to a control module via lead bodies, according to the invention.

FIG. 1 illustrates schematically one embodiment of an electrical stimulation system 100. The electrical stimulation system includes a control module (e.g., a stimulator or pulse generator) 102, a paddle body 104, and one or more lead bodies 106 coupling the control module 102 to the paddle body 104. The paddle body 104 and the one or more lead bodies 106 form a lead. The paddle body 104 typically includes an array of electrodes 134. The control module 102 typically includes an electronic subassembly 110 and an optional power source 120 disposed in a sealed housing 114. In FIG. 1, two lead bodies 106 are shown coupled to the control module 102.

The control module 102 typically includes one or more connector assemblies 144 into which the proximal end of the one or more lead bodies 106 can be plugged to make an electrical connection via connector contacts (e.g., 316 in FIGS. 3A-3B; and 340 of FIG. 3C) disposed in the connector assembly 144 and terminals (e.g., 310 in FIGS. 3A-3C) on each of the one or more lead bodies 106. The connector contacts are coupled to the electronic subassembly 110 and the terminals are coupled to the electrodes 134. In FIG. 1, two connector assemblies 144 are shown.

The one or more connector assemblies 144 may be disposed in a header 150. The header 150 provides a protective covering over the one or more connector assemblies 144. The header 150 may be formed using any suitable process including, for example, casting, molding (including injection molding), and the like. In addition, one or more lead extensions 324 (see FIG. 3C) can be disposed between the one or more lead bodies 106 and the control module 102 to extend the distance between the one or more lead bodies 106 and the control module 102.

Figure 2:
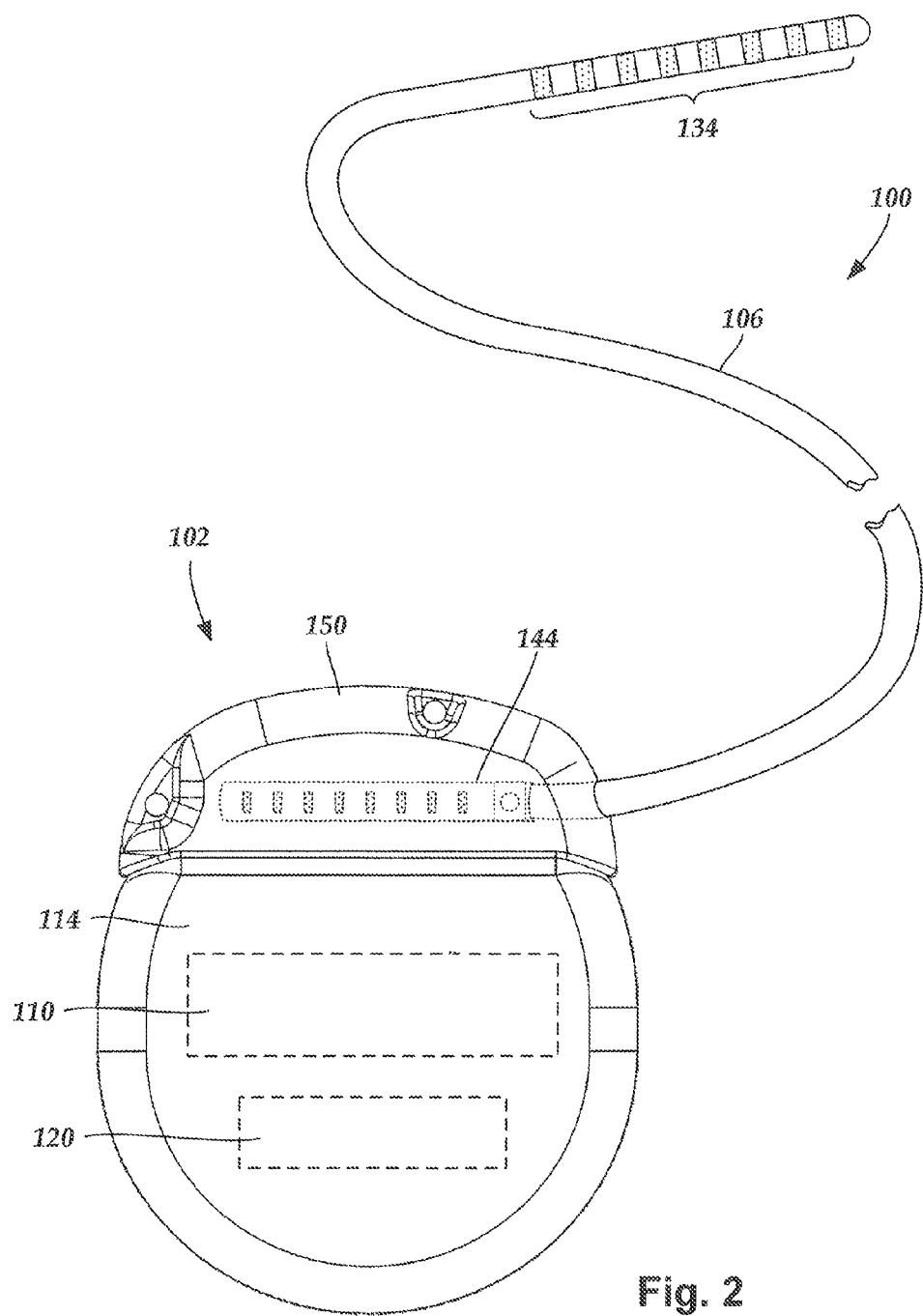
FIG. 2 is a schematic view of another embodiment of an electrical stimulation system that includes a percutaneous lead body coupled to the control module of FIG. 1, according to the invention.

It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of the lead body 106 forming a percutaneous lead, as illustrated in FIG. 2. A percutaneous lead may be isodiametric along the length of the lead body 106.

The electrical stimulation system or components of the electrical stimulation system, including one or more of the lead bodies 106, the control module 102, and, in the case of a paddle lead, the paddle body 104, are typically implanted into the body of a patient. The electrical stimulation system can be used for a variety of applications including, but not limited to, spinal cord stimulation, brain stimulation, neural stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, titanium, or rhenium.

The number of electrodes 134 in the array of electrodes 134 may vary. For example, there can be two, three, four, five, six, seven, eight, nine, ten, eleven, twelve, thirteen, fourteen, fifteen, sixteen, or more electrodes 134. As will be recognized, other numbers of electrodes 134 may also be used. In FIG. 1, sixteen electrodes 134 are shown. The electrodes 134 can be formed in any suitable shape including, for example, round, oval, triangular, rectangular, pentagonal, hexagonal, heptagonal, octagonal, or the like.

The electrodes of the paddle body 104 or one or more lead bodies 106 are typically disposed in, or separated by, a non-conductive, biocompatible material including, for example, silicone, polyurethane, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIGS. 3A-3C) are typically disposed at the proximal end of the one or more lead bodies 106 for connection to corresponding conductive contacts (e.g., 316 in FIGS. 3A-3B; and 340 of FIG. 3C) in connector assemblies (e.g., 144 in FIGS. 1-3C) disposed on, for example, the control module 102 (or to other devices, such as conductive contacts on a lead extension, an operating room cable, a splitter, an adaptor, or the like).

Conductive wires (not shown) extend from the terminals (e.g., 310 in FIGS. 3A-3C) to the electrodes 134. Typically, one or more electrodes 134 are electrically coupled to a terminal (e.g., 310 in FIGS. 3A-3C). In some embodiments, each terminal (e.g., 310 in FIGS. 3A-3C) is only coupled to one electrode 134.

The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more stylet lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. In at least one embodiment, the one or more lumens may be flushed continually, or on a regular basis, with saline, epidural fluid, or the like. In at least some embodiments, the one or more lumens can be permanently or removably sealable at the distal end.

As discussed above, the one or more lead bodies 106 may be coupled to the one or more connector assemblies 144 disposed on the control module 102. The control module 102 can include any suitable number of connector assemblies 144 including, for example, two three, four, five, six, seven, eight, or more connector assemblies 144. It will be understood that other numbers of connector assemblies 144 may be used instead. In FIG. 1, each of the two lead bodies 106 includes eight terminals that are shown coupled with eight conductive contacts disposed in a different one of two different connector assemblies 144.

Figure 3A:
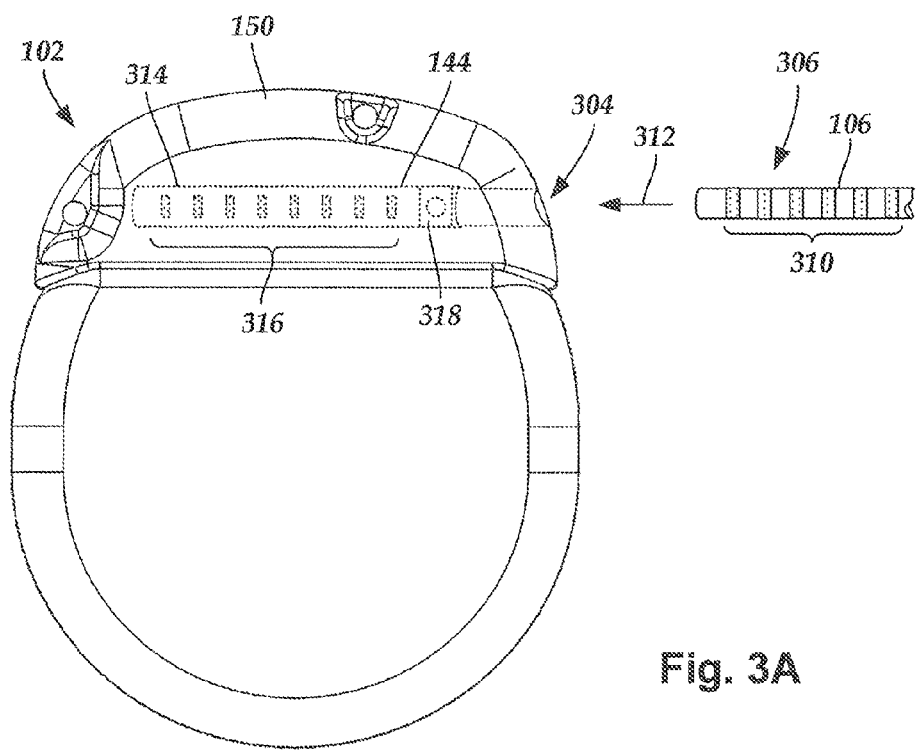
FIG. 3A is a schematic view of one embodiment of a connector assembly disposed in the control module of FIG. 1, the connector assembly configured and arranged to receive the proximal portion of one of the lead bodies of FIG. 1, according to the invention.
Figure 3B:
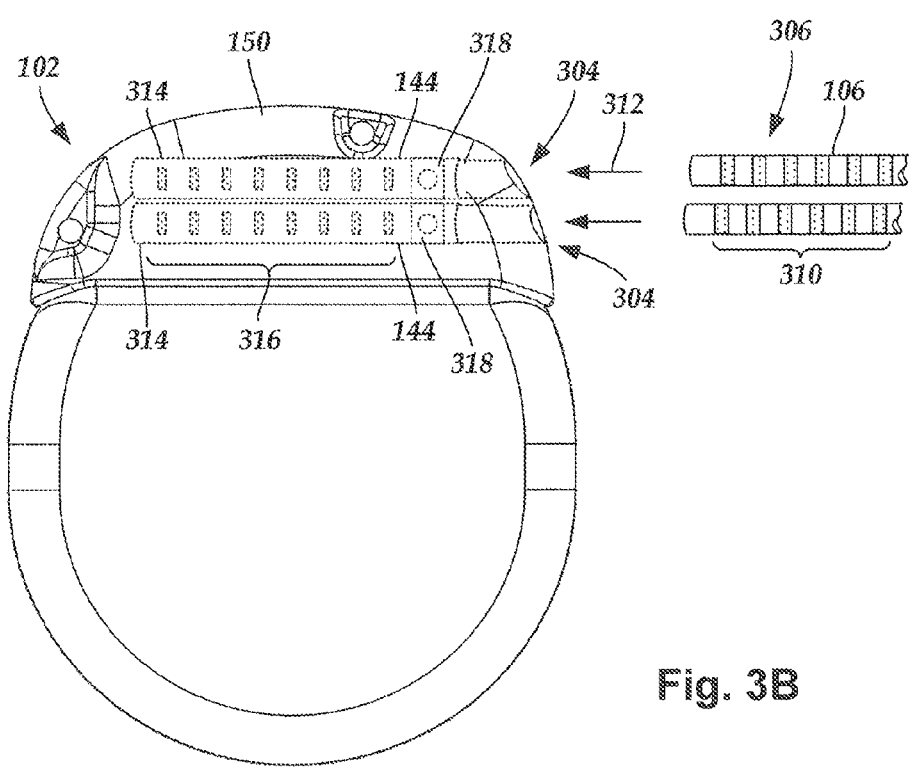
FIG. 3B is a schematic view of one embodiment of a plurality of connector assemblies disposed in the control module of FIG. 1, the connector assemblies configured and arranged to receive the proximal portions of the lead bodies of FIG. 1, according to the invention.

In at least some embodiments, leads are coupled to connectors disposed on control modules. FIG. 3A is a schematic perspective view of one embodiment of a single connector assembly 144 disposed on the control module 102. FIG. 3B is a schematic perspective view of one embodiment of a plurality of connector assemblies 144 disposed on the control module 102. In at least some embodiments, the control module 102 includes two connector assemblies 144. In at least some embodiments, the control module 102 includes four connector assemblies 144. In FIGS. 3A and 3B, the proximal ends 306 of one or more lead bodies 106 are shown configured and arranged for insertion to the control module 102. In FIGS. 3A and 3B, the one or more connector assemblies 144 are disposed in the header 150. In at least some embodiments, the header 150 defines one or more ports 304 into which a proximal end 306 of the one or more lead bodies 106 with terminals 310 can be inserted, as shown by directional arrows 312, in order to gain access to the connector contacts disposed in the one or more connector assemblies 144.

The one or more connector assemblies 144 each include a connector housing 314 and a plurality of connector contacts 316 disposed therein. Typically, the connector housing 314 defines a port (not shown) that provides access to the plurality of connector contacts 316. In at least some embodiments, one or more of the connector assemblies 144 further includes a retaining element 318 configured and arranged to fasten the corresponding lead body 308 to the connector assembly 144 when the lead body 106 is inserted into the connector assembly 144 to prevent undesired detachment of the lead body 106 from the connector assembly 144. For example, the retaining element 318 may include an aperture through which a fastener (e.g., a set screw, pin, or the like) may be inserted and secured against an inserted lead body or lead extension.

When the one or more lead bodies 106 are inserted into the one or more ports 304, the connector contacts 316 can be aligned with the terminals 310 disposed on the one or more lead bodies 106 to electrically couple the control module 102 to the electrodes (134 of FIG. 1) disposed at a distal end of the one or more lead bodies 106. Examples of connector assemblies in control modules are found in, for example, U.S. Pat. No. 7,244,150 and U.S. Patent Application Publication No. 2008/0071320, which are incorporated by reference.

Figure 3C:
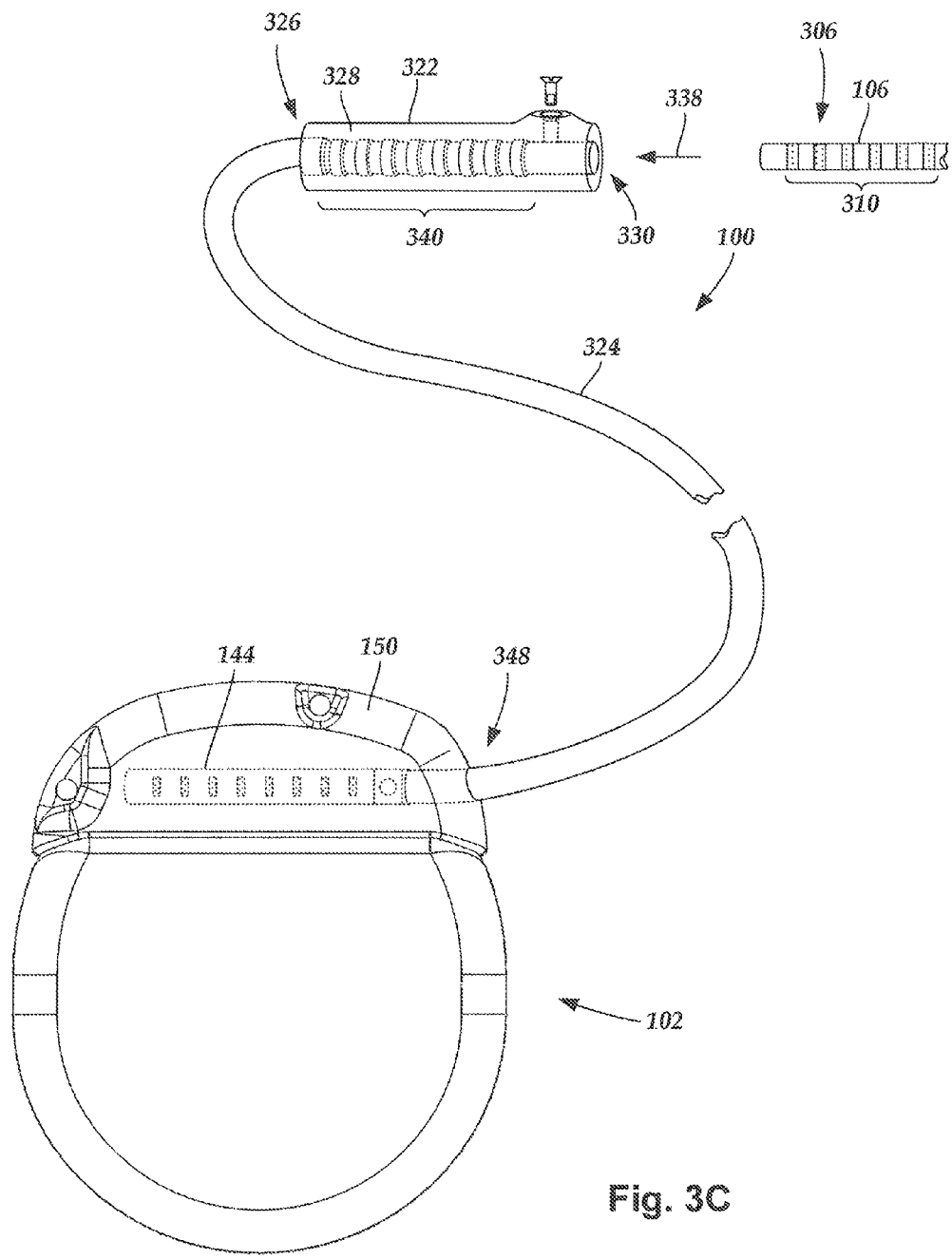
FIG. 3C is a schematic view of one embodiment of a proximal portion of one of the lead bodies of FIG. 1, a lead extension, and the control module of FIG. 1, the lead extension configured and arranged to couple the lead body to the control module, according to the invention.

In FIG. 3C, a lead extension connector assembly 322 is disposed on a lead extension 324. The lead extension connector assembly 322 is shown disposed at a distal end 326 of the lead extension 324. The lead extension connector assembly 322 includes a contact housing 328. The contact housing 328 defines at least one port 330 into which a proximal end 306 of the lead body 106 with terminals 310 can be inserted, as shown by directional arrow 338. The lead extension connector assembly 322 also includes a plurality of connector contacts 340. When the lead body 106 is inserted into the port 330, the connector contacts 340 disposed in the contact housing 328 can be aligned with the terminals 310 on the lead body 106 to electrically couple the lead extension 324 to the electrodes (134 of FIG. 1) disposed at a distal end (not shown) of the lead body 106.

The proximal end of a lead extension can be similarly configured and arranged as a proximal end of a lead body. The lead extension 324 may include a plurality of conductive wires (not shown) that electrically couple the connector contacts 340 to a proximal end 348 of the lead extension 324 that is opposite to the distal end 326. The conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a lead extension connector assembly disposed in another lead extension. In other embodiments (as shown in FIG. 3C), the proximal end 348 of the lead extension 324 is configured and arranged for insertion into the connector assembly 144 disposed on the control module 102.

Conventional electrical stimulation systems may be potentially unsafe for use when exposed to some types of electromagnetic induction or interference. For example, conventional electrical stimulation systems may be potentially unsafe for use when exposed to RF irradiation, such as during a magnetic resonance imaging ("MRI") procedure. A common cause of the electrical interaction between the electrical stimulation system and RF irradiation is common-mode coupling of the applied electromagnetic field. The interaction can be modeled as a series of distributed sources along the elongated conductive structures of the electrical stimulation system, such as leads, lead extensions, or conductors within leads or lead extensions. Common-mode induced RF currents may reach amplitudes of greater than one ampere in MRI environments. Such currents can cause heating and potentially disruptive voltages within electronic circuits. It will be understood that differential mode signals may also be a cause of electrical interaction and may also cause heating and potentially disruptive voltages within electronic circuits.

Figure 4A:
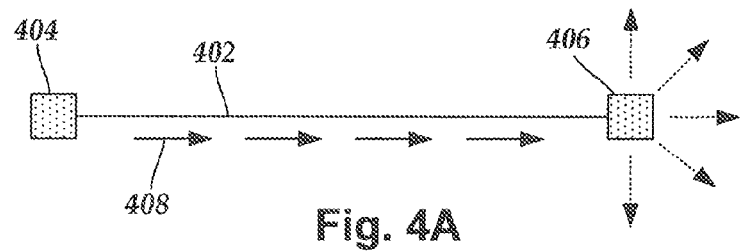
FIG. 4A is a schematic side view of one embodiment of a common-mode current propagating along an exemplary conductor of a lead towards an electrode of the lead, according to the invention.
Figure 4B:
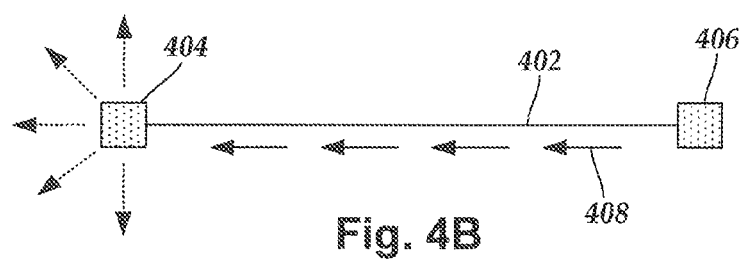
FIG. 4B is a schematic side view of one embodiment of a common-mode current propagating along the exemplary lead conductor of FIG. 4A, the common-mode current propagating towards a terminal of the lead, according to the invention.

FIG. 4A and FIG. 4B are schematic diagrams of embodiments of a conductor 402 suitable for use in a lead (or lead extension) of an electrical stimulation system. The conductor 402 extends between a terminal 404 and an electrode 406 (or a connector contact). When the conductor 402 is exposed to RF irradiation, such as when an implanted conductor 402 is in a patient undergoing an MRI procedure, a distributed electrical source (e.g., current, voltage), represented in FIGS. 4A and 4B as arrows 408, can be formed and distributed along the conductor 402 by the coupling of incident electrical fields with the conductor 402.

The electrical fields can become concentrated at the ends of the conductor 402, such as the electrode 406 (or connector contact) (see FIG. 4A), or the terminal 404 (see FIG. 4B), causing one or more undesired effects. Some of the undesired effects may include, for example, excessive heating that may potentially cause tissue damage, or induced currents (potentially causing heating, undesired electrical stimulation, device malfunction, or a combination thereof). During the implanted lifetime of an implanted electrical system, when electric fields become concentrated at a proximal end of a lead that is coupled to a control module, some of the undesired effects may additionally include, for example, undesired or unexpected operation of electronic components, or premature failure of electronic components.

To reduce the susceptibility of the electrical stimulation system to undesired electromagnetic induction or interference (e.g., RF irradiation), it may be advantageous to be able to electrically disconnect one or more electrical paths along the electrical stimulation system to form two or more electrically-conductive regions that are electrically isolated from one another. As herein described, the electrical stimulation system includes one or more electrical-propagation disconnecting features ("disconnecting features") for disconnecting one or more electrical paths along the electrical stimulation system, thereby potentially reducing the susceptibility of the electrical stimulation system to undesired RF irradiation. In some cases, current flow between the two or more electrically-conductive regions may be significantly disrupted. In other cases, current flow between the two or more electrically-conductive regions may be completely disrupted. In at least some embodiments, the current flow may be re-established (e.g., after a period of time, after an action by a user, or the like).

In some cases, the disconnecting features can be configured and arranged to mechanically move a lead relative to a connector assembly (e.g., on a control module, on a lead extension, or the like) such that an electrical connection (e.g., current propagation) between the lead and the connector assembly is severed, or at least significantly reduced. In some cases, the disconnecting features may include switches configured and arranged to electrically disable, or at least significantly reduce, an electrical connection between a connector assembly and an electronic subassembly of a control module when the switch is opened.

The disconnecting feature may provide advantages over conventional common-mode induced RF current suppressors. For example, in at least some embodiments the disconnecting feature does not rely on filtering circuitry (e.g., LC circuits, or the like) to suppress common-mode induced RF current. Therefore, RF current suppression may not be limited to discrete bandwidths. In some cases, the disconnecting feature may be frequency independent).

Additionally, safety margins for components of electrical stimulation systems (e.g., leads, lead extensions, control modules, or the like) can be determined at the component level, instead of at the system level, thereby potentially reducing complexity of safety calculations. This may be especially helpful when, as may sometimes be the case in practice, medical practitioners mix and match components of different electrical stimulation systems during an implantation procedure, thereby potentially rendering system-wide safety calculations ineffectual.

One or more disconnecting features can be used to split the electrical stimulation system into two or more independent electrically-conductive components, each of the two or more independent electrically-conductive components including one or more of a lead, a lead extension, and a control module. The one or more disconnecting features can be disposed on or in any suitable component of the electrical stimulation system. In some cases, one or more disconnecting features are disposed on one or more connector assemblies (e.g., of a lead extension, of a control module, of an adaptor, of a splitter, or the like), or the like. Optionally, the one of more disconnecting features are disposed in a housing of a control module.

The electrically-disconnected component can be either temporarily or permanently disconnected from other components of the electrical stimulation system. Optionally, the disconnecting feature can be configured and arranged to reconnect one or more disconnected (e.g., severed) electrical paths. The one or more disconnecting features can be activated either automatically or manually. In some cases, the one or more disconnecting features may be activated using a controller (e.g., a remote control, or the like).

Figure 5A:
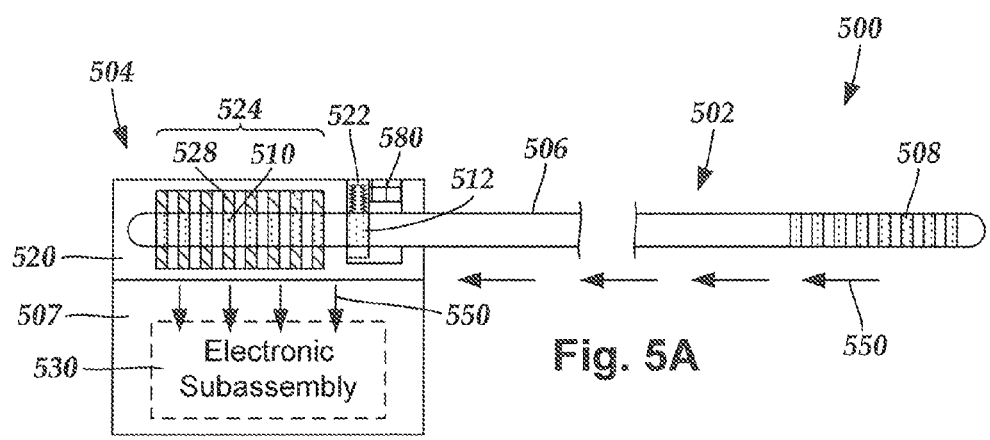
FIG. 5A is a schematic side view of one embodiment of one end of a lead disposed in a connector assembly of a control module, the connector assembly having a disconnecting feature in a de-activated position that enables a common-mode current propagating along the lead to propagate to the control module via an electrical connection between the lead and the connector assembly of the control module, according to the invention.
Figure 5B:
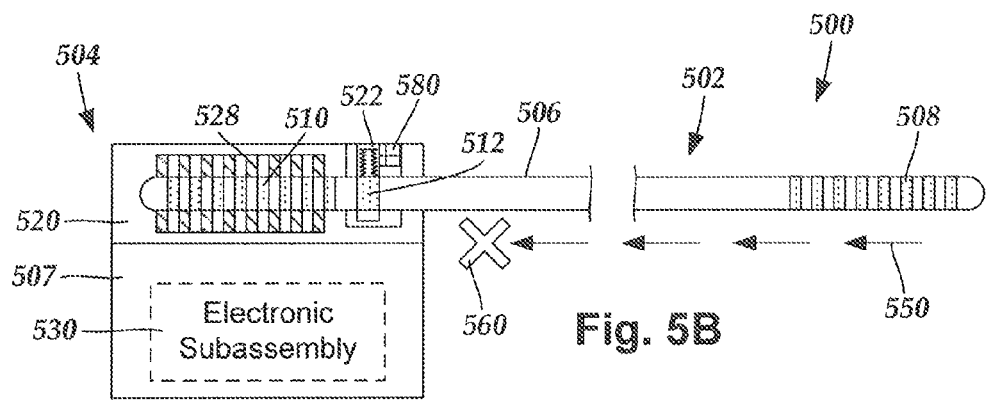
FIG. 5B is a schematic side view of one embodiment of the disconnecting feature of FIG. 5A transitioned to an activated position, the transition mechanically moving the lead of FIG. 5A relative the connector assembly of FIG. 5A to electrically disconnect the lead from the connector assembly, thereby disrupting propagation of the common-mode current of FIG. 5A between the lead and the control module, according to the invention.

In at least some embodiments, the disconnecting features are configured and arranged to mechanically move a lead relative to a connector assembly such that the electrical connection between the lead and the connector assembly is severed, or at least significantly reduced. FIG. 5A and FIG. 5B are schematic side views of one embodiment of an electrical stimulation system 500. The electrical stimulation system 500 includes a lead 502 and a control module 504. One end of the lead 502 is disposed in the control module 504. The lead 502 includes a lead body 506; electrodes, such as electrode 508, disposed at a distal end of the lead body 506; and terminals, such as terminal 510, disposed at a proximal end of the lead body 506. A retention sleeve 512 is also disposed on the proximal end of the lead body 506.

The control module 504 includes a connector assembly 520 for receiving the proximal end of the lead body 506 and a housing 507 that includes an electronic subassembly 530 for generating electrical pulses. The connector assembly 520 includes a retention block 522 for coupling with the retention sleeve 512 of the lead 502 and a connector block 524 that includes a plurality of connector contacts, such as connector contact 528, that are electrically coupled to the electronic subassembly 530. When the proximal end of the lead body 506 is disposed in the connector assembly 520 such that the terminals 510 of the lead 502 couple to the connector contacts 528 of the connector assembly 520, an electrical connection is established between the electrical subassembly 530 and the electrodes 508.

A disconnecting feature 580 can be actuated to mechanically move the lead 502 relative to the connector assembly 520 such that the electrical connection between the lead 502 and the connector assembly 520 is severed, or at least significantly reduced. The disconnecting feature 580 can be configured and arranged to transition from a first position (e.g., a de-activated position) to a second position (e.g., an activated position). In at least some embodiments, the disconnecting feature 580 can be configured and arranged to transition from the second position back to the first position. The transition can include any physical change in the disconnecting feature 580 (e.g., a movement, a shape change, an expansion, a contraction, or the like) that causes the lead 502 to move relative to the connector assembly 520.

In FIG. 5A, the disconnecting feature 580 is shown in a first position, where the terminals 510 of the lead 502 are electrically coupled to the connector contacts 528 of the connector assembly 520. Typically, the disconnecting feature 580 is in a first position during standard operation of the electrical stimulation system 500.

Thus, as shown in FIG. 5A, when the disconnecting feature 580 is in the first position, a common-mode current 550 propagating along the lead 502 is enabled to propagate across the electrical connection between the terminals 510 and the connector contacts 528, thereby potentially causing one or more deleterious effects to the electronic subassembly 530 (e.g., undesired or unexpected operation of electronic components, premature failure of electronic components, or the like).

In FIG. 5B, the disconnecting feature 580 has transitioned to a second position, thereby causing the lead 502 to move relative to the connector assembly 520. Consequently, the terminals 510 of the lead 502 have been electrically disconnected from the connector contacts 528 of the connector assembly 520. In which case, the lead 502 becomes electrically isolated from the control module 504. Consequently, the common-mode current 550 propagating along the lead 502 is prevented from propagating to the control module 504, as shown in FIG. 5B by an "X" 560. Additionally, common-mode currents (not shown) propagating along the control module 504 are prevented from propagating to the lead 502.

In FIGS. 5A and 5B, the disconnecting feature is shown disposed on a connector assembly of a control module. The disconnecting feature can be disposed on any suitable connector assembly of the electrical stimulation system including, for example, a connector assembly of a lead extension. FIG. 6 is a schematic view of one embodiment of the electrical stimulation system 500 with the disconnecting feature 580 disposed on a lead extension 602. The lead extension 602 is disposed between the lead 502 and the control module 504.

The lead extension 602 includes a connector assembly 620 configured and arranged to receive the lead 502. The connector assembly 620 includes connector contacts 628 configured and arranged to electrically couple with the terminals 510 of the lead 502. The lead extension 602 also includes a lead extension body 640 that is coupled to the connector assembly 620 and that includes lead extension terminals, such as lead extension terminal 650, configured and arranged to couple with connector contacts disposed on other connector assemblies (see e.g., connector assemblies 144, 322, 520, 620, 720, or the like). The lead extension 602 can be any suitable length. In some cases, the lead extension 602 has a length 680 that is no greater than 150 cm, 100 cm, 80 cm, 60 cm, 50 cm, 40 cm, 30 cm, 20 cm, 15 cm, 14 cm, 13 cm, 12 cm, 11 cm, 10 cm, 9 cm, 8 cm, 7 cm, 6 cm, 5 cm, or less. The electrical stimulation system 500 can include disconnecting members 580 on multiple components of the electrical stimulation system 500. For example, the electrical stimulation system 500 may include disconnecting members on both the control module connector assembly 520 and the lead extension connector assembly 620. In some cases, the electrical stimulation system 500 may include multiple lead extensions 602. In which case, one or more disconnecting members may be disposed on any suitable number of the multiple lead extensions 602.

The one or more disconnecting features can be used to mechanically move the lead relative to a connector assembly (e.g., of a control module, of a lead extension, or the like) of the electrical stimulation system in any suitable manner. FIG. 7A and FIG. 7B are schematic side views of one embodiment of one end of the lead 502 disposed in a connector assembly 720. In FIG. 7A, the terminals 510 of the lead 502 are shown aligned with connector contacts 728 of the connector assembly 720 such that an electrical connection is established between the lead 502 and the connector assembly 720. The retention sleeve 512 of the lead 502 is also aligned with a retention block 722 of the connector assembly 720. A fastener 702 (e.g., a screw, a pin, or the like) is disposed in the retention block 722 and is tightened against the retention sleeve 512 to prevent an undesired disconnection of the lead 502 from the connector assembly 720 during the implanted lifetime of the electrical stimulation system.

In one example of a narrow embodiment, the disconnecting feature 580 is coupled to the retention block 722 which, in turn, is disposed on the connector assembly 720 such that the retention block 722 is configured and arranged to mechanically move relative to the connector block 724 along an axis parallel to a longitudinal axis of the connector block 724. Thus, when the lead 502 is fastened to the retention block 722, physical movement of the retention block 722 relative to the connector block 724 causes a corresponding physical movement of the lead 502 relative to the connector block 724. The physical movement of the lead 502 relative to the relative to the connector block 724 causes the electrical connection between the terminals 510 and the connector contacts 728 to be severed, as shown in FIG. 7B.

In some cases, the physical movement of the lead 502 relative to the relative to the connector block 724 may be approximately equal to a width of the either (or both) the terminal or the connector contact. In some cases, the physical movement of the lead relative to the connector assembly significantly reduces the amount of physical contact between the terminals and the connector contacts. In other cases, the physical movement of the lead relative to the connector assembly terminals causes the connector contacts to be completely isolated from the terminals.

The transition of the disconnecting feature 580 can include any physical change in the disconnecting feature 580 (e.g., a movement, a shape change, an expansion, a contraction, or the like) that causes the lead 502 to move relative to the connector assembly 720. In FIGS. 7A and 7B, a contraction of the disconnecting feature 580 causes the electrical connection between the lead 502 and the connector assembly 720 to be severed. In alternate embodiments, expansion of the disconnecting feature 580 causes the electrical connection between the lead 502 and the connector assembly 720 to be severed.

In some cases, the disconnecting feature 580 mechanically moves the lead 502 relative to the connector assembly 720 by moving the lead 502. In some cases, the disconnecting feature 580 mechanically moves the lead 502 relative to the connector assembly 720 by moving the connector assembly 720. In some cases, disconnecting feature 580 mechanically moves the lead 502 relative to the connector assembly 720 by moving one or more structures of the connector assembly 720 either with or without also moving the lead 502. In at least some cases, the disconnecting feature 580 mechanically moves the lead 502 relative to the connector assembly 720 by moving the connector block 724 either with or without also moving the lead 502.

The disconnecting feature 580 can be implemented in any suitable manner. In some cases, the disconnecting feature 580 may include a motor (e.g., a piezo-electric-driven motor, or the like), a pressurized piston, or the like or combinations thereof. Actuation of the disconnecting feature 580 can be performed in any suitable manner. In some cases, actuation may occur automatically in response to an event (e.g., exposure to an electric field, exposure to a magnetic field, or the like). Optionally, one or more sensors (e.g., an electric field sensor, a magnetic field sensor, or the like) can be positioned in proximity to the disconnecting feature 580 and used to detect when actuation is to occur.

In some cases, actuation may be controllable via the electronic subassembly 530 of the control module 504. In other cases, actuation may occur in response to manual actuation. Manual actuation may involve either adjusting the disconnecting feature 580 directly (e.g., via a needle stick, via applied pressure from a position external to the patient, or the like), or indirectly (e.g., via the electronic subassembly 530, a remote control, or the like).

In some cases, actuation may be minimally invasive (e.g., a needle stick, applied pressure from a position external to the patient, or the like or combinations thereof). In other cases, actuation may be non-invasive (e.g., interaction with the disconnecting feature 580 from a location external to the patient, one or more software or firmware controlled methods, applied control signals directed to the disconnecting feature, physical interaction with a controller on the electrical stimulation system through patient tissue, or the like).

Figure 8:
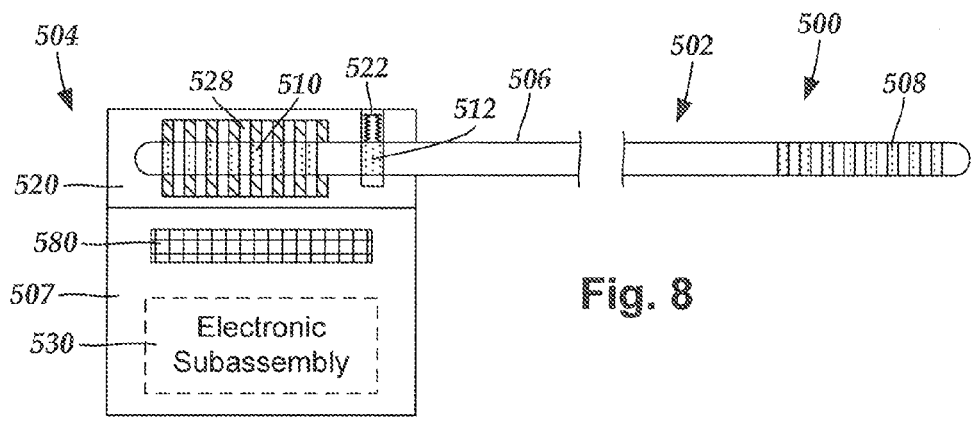
FIG. 8 is a schematic side view of one embodiment of a disconnecting feature disposed in a housing of the control module of FIG. 5A, according to the invention.

In some cases, disconnecting one or more electrical paths along the electrical stimulation system may not involve any physical or mechanical movement or rearrangement of components of the system. In at least some embodiments, one or more disconnecting features are disposed in the housing of the control module. FIG. 8 is a schematic side view of one embodiment of the disconnecting feature 580 disposed in the housing 507 of the control module 504. In some cases, the electrical stimulation system 500 may include any of the disconnecting features of FIGS. 5A-7B in combination with the disconnecting feature shown in FIG. 8.

The disconnecting feature 580 can be implemented in any suitable manner. In some cases, the disconnecting feature 580 includes a switch (e.g., a MEMS switch, a piezoelectric switch, a shape memory material switch, or the like). In some cases, the switch can be opened to disrupt an electrical connection between the connector contacts 528 and the electronic subassembly 530. In some cases, the switch can also be closed, for example, to create an alternative or parallel electrical routing.

When the disconnecting feature 580 includes a switch, the switch may be fabricated using micro fabrication techniques. When the disconnecting feature 580 includes a switch, the switch may, in some cases, be fabricated on a circuit board of the electronic subassembly 530. Optionally, a motor (or an actuator assembly) may be used to actuate the switch. The motor (or actuator assembly) may be located within the housing 114. In this manner the components used can be hermetically sealed inside of the housing 114. These switch features may actuate in a manner similar to the lead/header method described above, where two sets of electrical contacts are physically moved apart. When a motor is used, the motor may be a non-ferromagnetic motor. When a motor is used, the motor may be a piezo electric driven motor that is not susceptible to strong magnetic fields during operation.

Actuation of the switch can be performed in any suitable manner. In some cases, actuation may occur automatically in response to an event (e.g., exposure to an electric field, exposure to a magnetic field, or the like). In which case, one or more suitable sensors (e.g., electric field sensors, magnetic field sensors, or the like) may be disposed in proximity to the switch. Optionally, actuation may be controllable via the electronic subassembly 530 of the control module 504. In other cases, actuation may occur in response to manual actuation. Manual actuation may involve either actuating the disconnecting feature 580 directly (e.g., via a needle stick, via applied pressure from a position external to the patient, or the like), or indirectly (e.g., via the electronic subassembly 530, a remote control, physical interaction with the switch or a controller through patient tissue, or the like).

Figure 9:
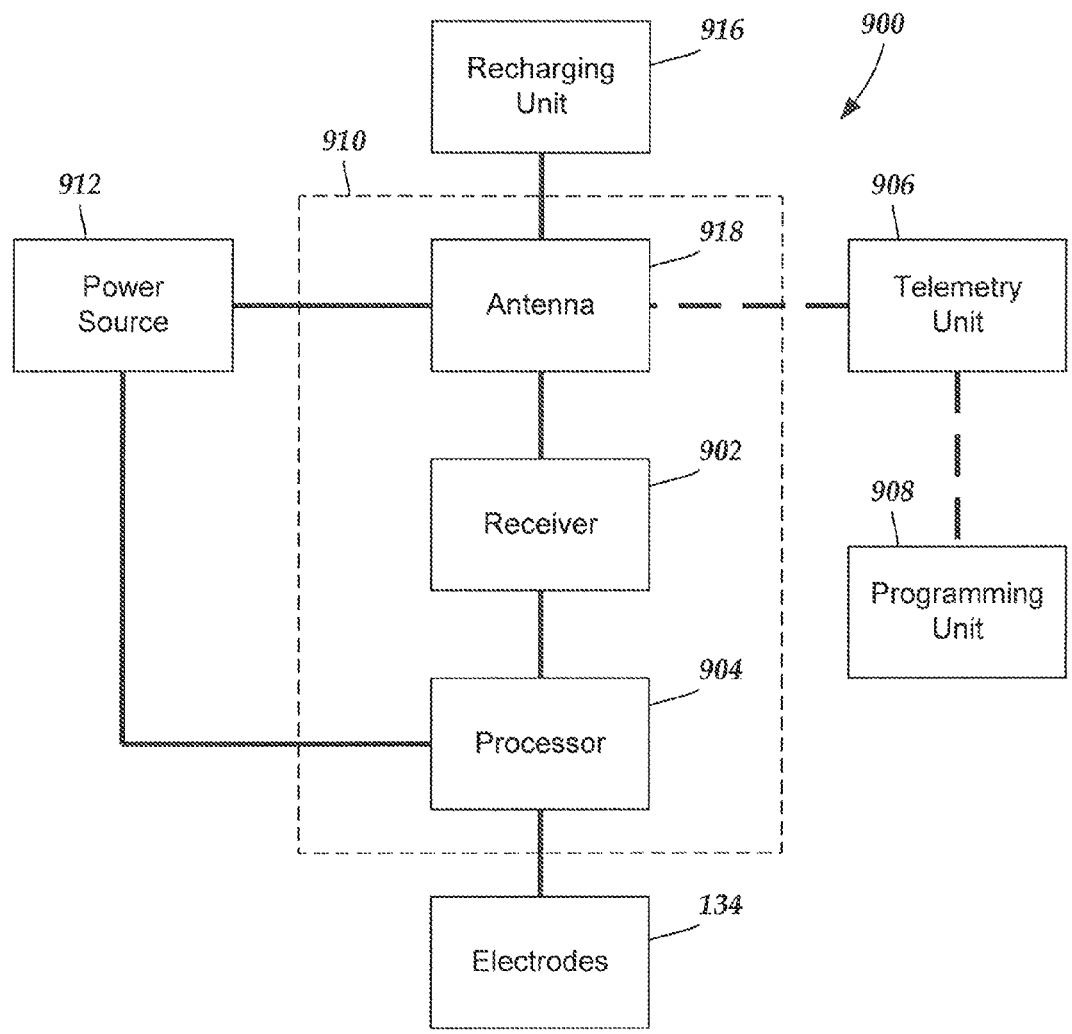
FIG. 9 is a schematic overview of one embodiment of components of a stimulation system, including an electronic subassembly disposed within a control module, according to the invention.

FIG. 9 is a schematic overview of one embodiment of components of an electrical stimulation system 900 including an electronic subassembly 910 disposed within a control module. It will be understood that the electrical stimulation system can include more, fewer, or different components and can have a variety of different configurations including those configurations disclosed in the stimulator references cited herein.

Some of the components (for example, power source 912, antenna 918, receiver 902, and processor 904) of the electrical stimulation system can be positioned on one or more circuit boards or similar carriers within a sealed housing of an implantable pulse generator, if desired. Any power source 912 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 918 or a secondary antenna. The external power source can be in a device that is mounted on the skin of the user or in a unit that is provided near the user on a permanent or periodic basis.

If the power source 912 is a rechargeable battery, the battery may be recharged using the optional antenna 918, if desired. Power can be provided to the battery for recharging by inductively coupling the battery through the antenna to a recharging unit 916 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 904 is generally included to control the timing and electrical characteristics of the electrical stimulation system. For example, the processor 904 can, if desired, control one or more of the timing, frequency, strength, duration, and waveform of the pulses. In addition, the processor 904 can select which electrodes can be used to provide stimulation, if desired. In some embodiments, the processor 904 may select which electrode(s) are cathodes and which electrode(s) are anodes. In some embodiments, the processor 904 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 908 that, for example, allows modification of pulse characteristics. In the illustrated embodiment, the processor 904 is coupled to a receiver 902 which, in turn, is coupled to the optional antenna 918. This allows the processor 904 to receive instructions from an external source to, for example, direct the pulse characteristics and the selection of electrodes, if desired.

In one embodiment, the antenna 918 is capable of receiving signals (e.g., RF signals) from an external telemetry unit 906 which is programmed by a programming unit 908. The programming unit 908 can be external to, or part of, the telemetry unit 906. The telemetry unit 906 can be a device that is worn on the skin of the user or can be carried by the user and can have a form similar to a pager, cellular phone, or remote control, if desired. As another alternative, the telemetry unit 906 may not be worn or carried by the user but may only be available at a home station or at a clinician's office. The programming unit 908 can be any unit that can provide information to the telemetry unit 906 for transmission to the electrical stimulation system 900. The programming unit 908 can be part of the telemetry unit 906 or can provide signals or information to the telemetry unit 906 via a wireless or wired connection. One example of a suitable programming unit is a computer operated by the user or clinician to send signals to the telemetry unit 906.

The signals sent to the processor 904 via the antenna 918 and receiver 902 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 900 to cease operation, to start operation, to start charging the battery, or to stop charging the battery. In other embodiments, the stimulation system does not include an antenna 918 or receiver 902 and the processor 904 operates as programmed.

Optionally, the electrical stimulation system 900 may include a transmitter (not shown) coupled to the processor 904 and the antenna 918 for transmitting signals back to the telemetry unit 906 or another unit capable of receiving the signals. For example, the electrical stimulation system 900 may transmit signals indicating whether the electrical stimulation system 900 is operating properly or not or indicating when the battery needs to be charged or the level of charge remaining in the battery. The processor 904 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An implantable electrical stimulation system comprising:
   a lead comprising
      a lead body having a distal end and a proximal end,
      a plurality of electrodes disposed on the distal end of the lead body,
      a plurality of terminals disposed on the proximal end of the lead body, and
      a plurality of conductors electrically coupling at least one of the electrodes to at least one of the terminals, the plurality of conductors extending along a longitudinal length of the lead body;
   a control module configured and arranged to electrically couple to the lead, the control module comprising
      a housing, and
      an electronic subassembly disposed in the housing;
   a connector assembly for receiving the lead body, the connector assembly comprising
      a connector assembly housing defining a port that is configured and arranged for receiving the proximal end of the lead body,
      a plurality of connector contacts disposed in the connector assembly housing and electrically coupled to the electronic subassembly, the plurality of connector contacts configured and arranged to align with the plurality of terminals such that an electrical connection is formed between the plurality of connector contacts and the plurality of terminals when the proximal end of the lead body is disposed in the port of the connector assembly, and a disconnecting feature comprising a switch disposed on or in the connector assembly, the switch configured and arranged to electrically disable, or at least significantly reduce, the electrical connection between the plurality of connector contacts and the electronic subassembly when the switch is opened by mechanically moving the proximal end of the lead body relative to the connector assembly housing to misalign the plurality of connector contacts from the plurality of terminals to sever, or at least significantly reduce, the electrical connection between the plurality of connector contacts and the plurality of terminals.

2. The system of claim 1, wherein the disconnecting feature is disposed in the control module housing.

3. The system of claim 1, wherein the switch is one of a MEMS switch, a piezoelectric switch, or a shape memory switch.

4. The system of claim 1, wherein the switch is disposed on a circuit hoard of the electronic subassembly.

5. The system of claim 1, wherein the disconnecting feature further comprises a motor configured and arranged to open the switch.

6. The system of claim 1, wherein the switch is configured and arranged to electrically re-establish the electrical connection between the plurality of connector contacts and the electronic subassembly when the switch is closed.

7. The system of claim 1, wherein the lead is a first lead and the connector assembly is a first connector assembly, and wherein the system further comprises a second lead and a second connector assembly configured and arranged to receive the second lead.

8. The system of claim 1, wherein the disconnecting feature is configured and arranged to electrically disable, or at least significantly reduce, the electrical connection between the electronic subassembly and at least one of the first lead or the second lead when the switch is opened.

9. The system of claim 1, wherein the connector assembly is disposed on the control module.

10. The system of claim 1, wherein the system further comprises at least one lead extension, each of the at least one lead extensions having a proximal end and a distal end, wherein the proximal end of at least one of the at least one lead extensions is configured and arranged for coupling to the control module and the distal end of at least one of the at least one lead extensions is configured and arranged for coupling to the lead.

11. The system of claim 10, wherein the connector assembly is disposed on the distal end of at least one of the at least one lead extensions.

12. The system of claim 1, further comprising a remote control for actuating the disconnecting feature.

13. The system of claim 1, wherein when the switch is implanted within a patient, the disconnecting feature is configured and arranged for actuation by physical interaction with the switch from a location that is external to the patient.

14. An implantable electrical stimulation system comprising:
a lead comprising
a lead body haying a distal end and a proximal end,
a plurality of electrodes disposed on the distal end of the lead body,
a plurality of terminals disposed on the proximal end of the lead body, and
a plurality of conductors electrically coupling at least one of the electrodes to at least one of the terminals, the plurality of conductors extending along a longitudinal length of the lead body;
a control module configured and arranged to electrically couple to the lead, the control module comprising
a housing, and
an electronic subassembly disposed in the housing;
a connector assembly for receiving the lead body, the connector assembly comprising
a connector assembly housing defining a port configured and arranged for receiving the proximal end of the lead body, and
a connector block disposed in the connector housing, the connector block con a plurality of connector contacts configured and arranged to align with the plurality of terminals of the lead such that an electrical connection is formed between the plurality of connector contacts and the plurality of terminals when the proximal end of the lead body is disposed in the port of the connector assembly, and
a disconnecting feature disposed on or in the connector assembly, the disconnecting feature configured and arranged to mechanically move the proximal end of the lead body relative to the connector block to misalign the plurality of connector contacts from the plurality of terminals to sever, or at least significantly reduce, the electrical connection between the plurality of connector contacts and the plurality of terminals.

15. The system of claim 14, wherein the disconnecting feature is configured and arranged to move the connector block.

16. The system of claim 14, wherein the disconnecting feature is configured and arranged to move the lead.

17. The system of claim 14, wherein the lead further comprises a retention sleeve disposed at the proximal end of the lead body, wherein the connector assembly further comprises a retention block configured and arranged to fasten to the retention sleeve of the lead body when the proximal end of the lead body is disposed in the connector assembly, and wherein the disconnecting feature is coupled to the retention block.

18. The system of claim 17, wherein the disconnecting feature is configured and arranged to move both the lead and the retention block relative to the connector block.

19. The system of claim 14, wherein the disconnecting feature comprises at least one of a motor or a piston.

20. A method of reducing susceptibility of an electrical stimulation system to undesired electromagnetic irradiation, the method comprising
inserting a lead into a connector assembly electrically coupled to a control module, the lead comprising a lead body comprising a plurality of electrodes disposed on a distal end of the lead body, a plurality of terminals disposed on a proximal end of the lead body, and a plurality of conductors electrically coupling at least one of the electrodes to at least one of the terminals, the connector assembly comprising a connector assembly housing defining a port, the port receiving the proximal end of the lead body when the lead is inserted into the connector assembly, and a connector block disposed in the connector housing, the connector block comprising a plurality of connector contacts that align with the plurality of terminals such that an electrical connection is formed between the plurality of connector contacts and the plurality of terminals when the lead is inserted into the connector assembly;

fastening a retention sleeve of the lead to a retention block of the connector assembly, wherein the retention block is configured and arranged to move relative to the connector block; and mechanically moving the proximal end of the lead body relative to the connector block using a disconnecting feature disposed on or in the connector assembly, the mechanical movement misaligning the plurality of connector contacts from the plurality of terminals such that the electrical connection between the plurality of connector contacts and the plurality of terminals is severed, or at least significantly reduced.

* * * * *